United States Patent
Collis et al.

(10) Patent No.: US 7,601,491 B2
(45) Date of Patent: Oct. 13, 2009

(54) PRETREATMENT METHOD FOR EXTRACTION OF NUCLEIC ACID FROM BIOLOGICAL SAMPLES AND KITS THEREFOR

(75) Inventors: Matthew P. Collis, Seven Valleys, PA (US); Donald W. Copertino, Catonsville, MD (US); Karen Eckert, Perry Hall, MD (US); Thomas L. Fort, Finksburg, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1095 days.

(21) Appl. No.: 10/359,179

(22) Filed: Feb. 6, 2003

(65) Prior Publication Data

US 2004/0157218 A1    Aug. 12, 2004

(51) Int. Cl.
*C12Q 1/68*     (2006.01)
*C07H 21/00*    (2006.01)
*C07K 14/00*    (2006.01)

(52) U.S. Cl. .................. 435/6; 536/22.1; 530/300
(58) Field of Classification Search .............. 435/6; 530/300; 536/22.1
See application file for complete search history.

(56) References Cited

U.S. PATENT DOCUMENTS

| | | | |
|---|---|---|---|
| 3,797,202 A | 3/1974 | Neulander et al. | |
| 3,970,518 A | 7/1976 | Giaever | |
| 3,985,649 A | 10/1976 | Eddelman | |
| 4,018,886 A | 4/1977 | Giaever | |
| 4,141,687 A | 2/1979 | Forrest et al. | |
| 4,230,685 A | 10/1980 | Senyei et al. | |
| 4,272,510 A | 6/1981 | Smith et al. | |
| 4,672,040 A | 6/1987 | Josephson | |
| 4,695,393 A | 9/1987 | Whitehead et al. | |
| 4,774,265 A | 9/1988 | Ugelstad et al. | |
| 4,855,045 A | 8/1989 | Reed | |
| 4,900,677 A | 2/1990 | Hewitt | |
| 4,910,148 A | 3/1990 | Sorensen et al. | |
| 4,923,978 A | 5/1990 | McCormick | |
| 4,935,147 A | 6/1990 | Ullman et al. | |
| 4,935,342 A | 6/1990 | Seligson et al. | |
| 4,946,952 A | 8/1990 | Kiefer | |
| 4,988,618 A | 1/1991 | Li et al. | |
| 5,010,183 A * | 4/1991 | Macfarlane ................. | 536/25.4 |
| 5,043,070 A | 8/1991 | Hwang | |
| 5,076,950 A | 12/1991 | Ullman et al. | |
| 5,084,169 A | 1/1992 | Noble et al. | |
| 5,129,936 A | 7/1992 | Wilson | |
| 5,130,423 A | 7/1992 | Van Ness et al. | |
| 5,167,811 A | 12/1992 | Graves et al. | |
| 5,234,809 A | 8/1993 | Boom et al. | |
| 5,242,833 A | 9/1993 | Lawlor et al. | |
| 5,279,936 A | 1/1994 | Vorpahl | |
| 5,318,914 A | 6/1994 | Matte et al. | |
| 5,336,760 A | 8/1994 | Hardwick et al. | |
| 5,340,749 A | 8/1994 | Fujiwara et al. | |
| 5,370,993 A | 12/1994 | Tarnowski et al. | |
| 5,386,024 A | 1/1995 | Kacian et al. | |
| 5,395,688 A | 3/1995 | Wang et al. | |
| 5,422,279 A | 6/1995 | Lawlor et al. | |
| 5,433,847 A | 7/1995 | Rice | |
| 5,438,128 A | 8/1995 | Nieuwkerk et al. | |
| 5,464,752 A | 11/1995 | Kortright et al. | |
| 5,474,914 A | 12/1995 | Spaete | |
| 5,491,068 A | 2/1996 | Benjamin et al. | |
| 5,512,439 A | 4/1996 | Hornes et al. | |
| 5,518,890 A | 5/1996 | Starkweather et al. | |
| 5,523,231 A | 6/1996 | Reeve | |
| 5,536,644 A | 7/1996 | Ullman et al. | |
| 5,541,072 A | 7/1996 | Wang et al. | |
| 5,543,289 A | 8/1996 | Miltenyi | |
| 5,582,988 A | 12/1996 | Backus et al. | |
| 5,595,913 A | 1/1997 | Lawlor et al. | |
| 5,625,053 A | 4/1997 | Kresheck et al. | |
| 5,637,687 A * | 6/1997 | Wiggins .................... | 536/25.4 |
| 5,646,001 A | 7/1997 | Terstappen et al. | |
| 5,647,994 A | 7/1997 | Tuunanen et al. | |
| 5,652,141 A | 7/1997 | Henco et al. | |
| 5,652,348 A | 7/1997 | Burton et al. | |
| 5,665,554 A | 9/1997 | Reeve et al. | |
| 5,674,997 A | 10/1997 | Woodard et al. | |
| 5,681,478 A | 10/1997 | Lea et al. | |
| 5,681,946 A | 10/1997 | Reeve | |
| 5,684,712 A | 11/1997 | Goffe et al. | |
| 5,693,785 A | 12/1997 | Woodard et al. | |
| 5,695,946 A | 12/1997 | Benjamin et al. | |
| 5,705,062 A | 1/1998 | Knobel | |
| 5,705,628 A | 1/1998 | Hawkins | |
| 5,763,203 A | 6/1998 | Ugelstad et al. | |
| 5,766,852 A | 6/1998 | Down et al. | |
| 5,773,307 A | 6/1998 | Colin et al. | |
| 5,786,208 A | 7/1998 | Clark et al. | |
| 5,834,197 A | 11/1998 | Parton | |
| 5,897,783 A | 4/1999 | Howe et al. | |
| 5,907,035 A | 5/1999 | Guinn | |
| 5,916,539 A | 6/1999 | Pilgrimm | |

(Continued)

FOREIGN PATENT DOCUMENTS

EP         0 261 956         3/1988

(Continued)

OTHER PUBLICATIONS

Stratagen catalog, p. 39, 1988.*

(Continued)

*Primary Examiner*—Jezia Riley
(74) *Attorney, Agent, or Firm*—Allan M. Kiang

(57) ABSTRACT

The present invention relates to methods for pretreating biological samples for extraction of nucleic acid therefrom The present invention employs a combination of at least one protein denaturant with one or more of the following elements to form a reaction mixture for extraction of nucleic acid: (1) at least one aprotic solvent, (2) stepwise heating, and (3) sample dilution.

25 Claims, No Drawings

U.S. PATENT DOCUMENTS

| | | | |
|---|---|---|---|
| 5,922,284 A | 7/1999 | Kinoshita et al. | |
| 5,925,573 A | 7/1999 | Colin et al. | |
| 5,928,958 A | 7/1999 | Pilgrimm | |
| 5,945,525 A | 8/1999 | Uematsu et al. | |
| 5,955,268 A | 9/1999 | Granados et al. | |
| 5,973,138 A | 10/1999 | Collis | |
| 5,981,235 A | 11/1999 | Shultz et al. | |
| 5,990,302 A | 11/1999 | Kuroita et al. | |
| 5,998,224 A | 12/1999 | Rohr et al. | |
| 6,008,002 A | 12/1999 | Bodey | |
| 6,020,210 A | 2/2000 | Miltenyi | |
| 6,020,211 A | 2/2000 | Tuunanen | |
| 6,024,881 A | 2/2000 | Just | |
| 6,027,945 A | 2/2000 | Smith et al. | |
| 6,033,574 A | 3/2000 | Siddiqi | |
| 6,040,192 A | 3/2000 | Tuunanen et al. | |
| 6,096,554 A | 8/2000 | Tajima | |
| 6,099,738 A | 8/2000 | Wechsler et al. | |
| 6,133,037 A | 10/2000 | Tajima | |
| 6,143,578 A | 11/2000 | Bendele et al. | |
| 6,146,511 A * | 11/2000 | Slater et al. | 204/457 |
| 6,187,270 B1 | 2/2001 | Schmitt et al. | |
| 6,210,881 B1 | 4/2001 | Little et al. | |
| 6,231,760 B1 | 5/2001 | Siddiqi | |
| 6,265,164 B1 | 7/2001 | Han et al. | |
| 6,294,342 B1 | 9/2001 | Rohr et al. | |
| 6,355,792 B1 | 3/2002 | Michelsen et al. | |
| 6,383,393 B1 | 5/2002 | Colpan et al. | |
| 6,410,725 B1 * | 6/2002 | Scholl et al. | 536/25.42 |
| 6,433,160 B1 | 8/2002 | Collis | |
| 6,534,262 B1 | 3/2003 | McKernan et al. | |
| 6,617,103 B1 | 9/2003 | Kessous et al. | |
| 6,632,438 B2 | 10/2003 | Paoletti et al. | |
| 6,672,458 B2 | 1/2004 | Hansen et al. | |
| 7,001,724 B1 * | 2/2006 | Greenfield | 435/6 |
| 2001/0018513 A1 | 8/2001 | Baker | |
| 2002/0068821 A1 | 6/2002 | Gundling | |
| 2002/0106686 A1 | 8/2002 | McKernan | |
| 2003/0008320 A1 | 1/2003 | Baker | |
| 2003/0017959 A1 | 1/2003 | Baeck et al. | |
| 2003/0054395 A1 | 3/2003 | Baker | |
| 2003/0130499 A1 | 7/2003 | Baker | |
| 2003/0178309 A1 | 9/2003 | Huang et al. | |
| 2003/0199078 A1 | 10/2003 | Kleiber et al. | |
| 2004/0029260 A1 | 2/2004 | Hansen et al. | |
| 2004/0157219 A1 | 8/2004 | Lou et al. | |
| 2004/0157223 A1 | 8/2004 | Lou et al. | |
| 2005/0239091 A1 | 10/2005 | Collis et al. | |
| 2006/0030056 A1 | 2/2006 | Fort et al. | |
| 2006/0105468 A1 * | 5/2006 | Winkler et al. | 436/174 |

FOREIGN PATENT DOCUMENTS

| | | |
|---|---|---|
| EP | 0 268 946 | 6/1988 |
| EP | 0 389 063 | 9/1990 |
| EP | 0 265 244 | 9/1992 |
| EP | 0 209 490 | 10/1992 |
| EP | 0 512 767 | 11/1992 |
| EP | 0 580 305 | 1/1994 |
| EP | 0 741 141 | 11/1996 |
| EP | 0 757 106 | 2/1997 |
| EP | 0 818 461 | 1/1998 |
| EP | 0 819 696 | 1/1998 |
| EP | 0 905 520 | 3/1999 |
| EP | 0 919 285 | 6/1999 |
| EP | 0 937 497 | 8/1999 |
| EP | 1 002 860 | 5/2000 |
| EP | 1 081 234 | 3/2001 |
| EP | 0 691 541 | 4/2002 |
| EP | 1 234 832 | 8/2002 |
| EP | 1 260 583 | 11/2002 |
| EP | 1 260 595 | 11/2002 |
| EP | 1 589 105 | 10/2005 |
| JP | 10-081507 | 3/1998 |
| JP | 10-214710 | 8/1998 |
| WO | WO 88/06633 | 9/1988 |
| WO | WO 88/09201 | 12/1988 |
| WO | WO 90/06042 | 6/1990 |
| WO | WO 90/06045 | 6/1990 |
| WO | WO 91/12079 | 8/1991 |
| WO | WO 92/07863 | 5/1992 |
| WO | WO 94/11103 | 5/1994 |
| WO | WO 95/01359 | 1/1995 |
| WO | WO 95/06652 | 3/1995 |
| WO | WO-96/09379 | 3/1996 |
| WO | WO 96/17959 | 6/1996 |
| WO | WO 96/18731 | 6/1996 |
| WO | WO 97/42342 | 11/1997 |
| WO | WO 98/04730 | 2/1998 |
| WO | WO 98/31461 | 7/1998 |
| WO | WO 98/31840 | 7/1998 |
| WO | WO 98/51693 | 11/1998 |
| WO | WO 99/29703 | 6/1999 |
| WO | WO 99/59695 | 11/1999 |
| WO | WO 99/61603 | 12/1999 |
| WO | WO 00/70040 | 11/2000 |
| WO | WO 01/14590 | 3/2001 |
| WO | WO 01/45522 | 6/2001 |
| WO | WO 01/46404 | 6/2001 |
| WO | WO 01/53525 | 7/2001 |
| WO | WO 01/60517 | 8/2001 |
| WO | WO 02/29406 | 4/2002 |
| WO | WO 02/48164 | 6/2002 |
| WO | WO 2004/053115 | 6/2004 |
| WO | WO 2006/017427 | 2/2006 |
| WO | WO 2006/020280 | 2/2006 |

OTHER PUBLICATIONS

Chomczynski, "Solubilization in Formamide Protects RNA from Degradation," *Nucleic Acids Research*, 1992, vol. 20, No. 14, pp. 3791-3792.

Sambrook et al., Molecular Cloning: A Laboratory Manual, "Commonly Used Techniques in Molecular Cloning," vol. 3, Appendix A8, 3rd Ed., Cold Springs Press, 2001.

Aquino et al., "Cytomegalovirus Infection in Renal Transplant Recipients Diagnosed by Nested-PCR," *Brazilian Journal of Medical and Biological Research*, 2001, vol. 34, No. 1, pp. 93-101.

Binder et al., "Identification of Human Cytomegalovirus Variants by Analysis of Single Strand Conformation Polymorphism and DNA Sequencing of the Envelope Glycoprotein B Gene Region-Distribution Frequency in Liver Transplant Recipients," *Journal of Virological Methods*, 1999, vol. 78, Nos. 1-2, pp. 153-162.

Bottcher et al., "Automated Free-Solution Isotachophoresis: Instrumentation and Fractionation of Human Serum Proteins," *Electrophoresis*, 1998, vol. 19, pp. 1110-1116.

S. Chou, "Differentiation of Cytomegalovirus Strains by Restriction Analysis of DNA Sequences Amplified from Clinical Specimens," *The Journal of Infectious Diseases*, 1990, vol. 162, pp. 738-742.

C. Coty, "Mass Spec Sample Prep: The Pure Advantage," *Genomics and Proteomics*, (2002).

Dauer et al., "High Gradient Magnetic Separation of Yeast," *Biotechnology and Bioengineering*, 1991, vol. 37, pp. 1021-1028.

Faggi et al., "Use of Magnetic Beads to Extract Fungal DNA," *Mycoses*, 2005, vol. 48, No. 1, pp. 3-7.

Friesen, A.D., "Chromatographic Methods of Fractionation," *Develop. Biol. Standard*, 1987, vol. 67, pp. 3-13.

Kislinger et al., "PRISM, A Generic Large Scale Proteomic Investigation Strategy for Mammals," *Molecular and Cellular Proteomics*, 2003, vol. 2.2, pp. 96-106.

Lopez et al., "High-Throughout Profiling of the Mitochondrial Proteome Using Affinity Fractionation and Automation," *Electrophoresis*, 2000, vol. 21, pp. 3427-3440.

Macrae et al. "Removal of Bacteria from Water by Adsorption to Magnetite," *Water Res.*, 1984, vol. 18, No. 11, pp. 1377-1380.

Macrae et al., "Factors Influencing the Adsorption of Bacteria to Magnetite in Water and Wastewater," *Water Res.*, 1983, vol. 17, No. 3, pp. 271-277.

Musial et al. "Detection of *Cryptosporidium* in Water by Using Polypropylene Cartridge Filters," *Applied and Environmental Microbiology*, 1987, vol. 53, No. 4, pp. 687-692.

Olsvik et al., "Magnetic Separation Techniques in Diagnostic Microbiology," *Clinical Microbiology Reviews*, 1994, vol. 7, No. 1, pp. 43-54.

Sadler et al., "Glycosidase Activities of *Bacillus anthracis*," *Journal of Clinical Microbiology*, 1984, vol. 19, No. 5, pp. 594-598.

Schoenfeld et al., "Effects of Bacterial Strains Carrying the *endA1* Genotype on DNA Quality Isolated with Wizard™ Plasmid Purification Systems," *Promega Notes Magazine*, 1995, No. 53, pp. 12-21.

Wagner et al., "An Automated On-Line Multidimensional HPLC System for Protein and Peptide Mapping with Integrated Sample Preparation," *Analytical Chemistry*, 2002, vol. 74, No. 4, pp. 809-820.

Zborowski et al., "Quantitative Separation of Bacteria in Saline Solution Using Lanthanide Er(III) and a Magnetic Field", *Journal of General Microbiology*, 1992, vol. 138, pp. 63-68.

Zhou et al., "Fast Detection of Human Cytomegalovirus and Differentiation of Glycoprotein B and H Genotypes by PCR-Assisted Reverse Hybridization," *China J. Microbiol. Immunol.*, 2002, vol. 22, No. 4, pp. 456-460.

Yang et al., "Enzyme Electrodes with Glucose Oxidase Immobilized on Stöber Glass Beads," *Analytical Letters*, 1995; 28(14):2439-2457.

\* cited by examiner

PRETREATMENT METHOD FOR EXTRACTION OF NUCLEIC ACID FROM BIOLOGICAL SAMPLES AND KITS THEREFOR

FIELD OF THE INVENTION

The present invention relates to methods of treating biological samples, such as plasma and blood samples, for analysis. More specifically, the invention relates to biological sample processing methods that are compatible with subsequent nucleic acid analysis, such as hybridization, amplification and detection.

BACKGROUND OF THE INVENTION

Nucleic acid-based genetic methods for identification of microorganisms have greatly reduced the time and labor involved in clinical diagnosis. Such methods include, for example, nucleic acid hybridization (e.g., Southerns/microarrays and slot blots), nucleotide sequencing, nucleic acid cloning techniques, restriction digestion of nucleic acids and nucleic acid amplification. In particular, nucleic acid amplification has provided means for rapid, sensitive and specific identification of microorganisms by amplification and detection of specific genes or gene fragments. For use as diagnostic methods, it is of particular interest to apply these nucleic acid analyses to biological samples such as plasma and whole blood samples. Prior to the availability of nucleic acid-based methods for detection and identification of microorganisms, plasma or blood samples were analyzed for the presence of microorganisms by blood culturing. However, processing of clinical samples for nucleic acid analyses requires different criteria than sample processing for culturing. For example, nucleic acids must be released from the microorganism in a form suitable for the analysis; nucleic acids must be present in a composition with the appropriate components, ionic strength and pH for the biochemical reactions of the analysis; and inhibitors of the reactions such as nucleases, if present in the clinical sample or introduced during sample processing, must be removed or rendered non-inhibitory.

One potential biochemical detection method involves the use of nucleic acid hybridization. The sequence specificity embodied in nucleic acids makes it possible to differentiate virtually any two species by nucleic acid hybridization. Standard techniques for detection of specific nucleotide sequences generally employ nucleic acids that have been purified away from cellular proteins and other cellular contaminants. The most common method of purification involves lysing the cells with sodium dodecyl sulfate (SDS), digesting with proteinase K (ProK), and removing residual proteins and other molecules by extracting with organic solvents such as phenol, chloroform, and isoamylalcohol.

Endogenous nucleases released during cell solubilization can frustrate efforts to recover intact nucleic acids, particularly ribonucleic acids (RNA). While deoxyribonucleases (DNases) are easily inactivated by the addition of chelating agents to the lysis solution, ribonucleases (RNases) are far more difficult to eliminate. RNases are ubiquitous, being present even in the oil found on human hands. Accordingly, protecting against RNase is a commonly acknowledged aspect of any standard RNA preparation technique. The standard procedure for preparing laboratory stocks of pancreatic RNase is to boil a solution of the enzyme for 15 minutes. The purpose of this treatment is to destroy all traces of contaminating enzyme activity because other enzymes cannot survive boiling.

Sambrook, et al., Molecular Cloning, 3$^{rd}$ Edition (2001), a compendium of commonly followed laboratory practices, recommends extensive precautions to avoid RNase contamination in laboratories. Such precautions include preparing all solutions that will contact RNA using RNase-free glassware, autoclaved water, and chemicals reserved for work with RNA that are dispensed exclusively with baked spatulas. Besides purging laboratory reagents of RNase, RNase inhibitors are typically included in lysis solutions. These are intended to destroy endogenous RNases that generally become activated during cell lysis. Also, it is common practice to solubilize RNA in diethyl pyrocarbonate (DEPC)-treated water. Moreover, in an attempt to improve the handling of RNA samples, formamide has been tested as a solubilizing agent for the long-term storage of RNA. Chomczynski, P., *Nucleic Acids Research* 20, 3791-3792 (1992).

Protecting against RNase is cumbersome and costly, and typical extraction procedures require the handling of caustic solvents, access to water baths, fume hoods, and centrifuges, and even the storage and disposal of hazardous wastes. The direct analysis of unfractionated solubilized biological samples would avoid the cost and inconvenience of these purification techniques.

In view of the foregoing, there exists a need for a simple and rapid method by which biological samples such as plasma and blood may be treated for the extraction therefrom of nucleic acid for analysis.

SUMMARY OF THE INVENTION

The present invention addresses the need for a simple and rapid method to treat biological samples such as plasma and blood for extraction of nucleic acid therefrom. In one embodiment, the method of the present invention pretreats biological samples for extraction of nucleic acid therefrom by mixing the biological samples with at least one protein denaturant and by stepwise heating the mixture in a temperature range of from about 55° C. to about 85° C. to form a reaction mixture. In another embodiment, the method of the present invention pretreats the biological samples by mixing the biological samples with at least one protein denaturant in a temperature range from about 55° C. to about 85° C. to form a reaction mixture and by diluting the reaction mixture with an aqueous solution or an aprotic solvent. Yet in another embodiment, the method of the present invention pretreats biological samples for extraction of nucleic acid therefrom by treating the samples with at least one protein denaturant and at least one aprotic solvent at or above about 4° C. to form a reaction mixture for nucleic acid analysis. In a preferred embodiment, the method of the present invention pretreats biological samples by treating the samples with at least one protein denaturant and at least one aprotic solvent at or above about 25° C. In an exemplary embodiment of the present invention, ProK is used as the protein denaturant, formamide is used as the aprotic solvent, and the treatment is conducted at a temperature in the range of about 55° C. to about 85° C. for about 30 minutes.

DETAILED DESCRIPTION OF THE INVENTION

As used herein, the terms "purifying" and "purification" also include extracting/extraction and isolating/isolation.

The present invention is a composition and method of treating biological samples such as, for example, plasma and whole blood samples, for extraction of nucleic acid therefrom. The present invention employs a combination of at least one protein denaturant with one or more of the following elements to form a reaction mixture for extraction of nucleic acid: (1) at least one aprotic solvent, (2) stepwise heating, and (3) sample dilution.

The biological samples used according to the present invention may be any biological material containing nucleic acid such as, for example, clinical, forensic or environmental samples. These samples may contain any viral or cellular material, including prokaryotic and eukaryotic cells, viruses, bacteriophages, mycoplasms, protoplasts and organelles. Such biological materials may comprise all types of mammalian and non-mammalian animal cells, plant cells, algae including blue-green algae, fungi, bacteria, yeast and protozoa. Representative examples include blood and blood-derived products such as whole blood, plasma and serum; clinical specimens such as semen, urine, feces, sputa, tissues, cell cultures and cell suspensions, nasopharangeal aspirates and swabs, including endocervical, vaginal, occular, throat and buccal swabs; and other biological samples such as finger nails, skin, hair and cerebrospinal fluid or other body fluid.

The protein denaturant is a reagent that is capable of, by itself or when combined with other protein denaturants and/or aprotic solvents, disrupting the protein membranes or walls of cells, virions, DNase or RNase, causing protein denaturation and organism lysis and releasing nucleic acid in biological samples. Protein denaturants are well known in the art, and may be purchased from known vendors or prepared using well-known standard techniques. Protein denaturants that are useful in the present invention include proteolytic enzymes, such as ProK, pronase, pepsin, trypsin, chymotrypsin, carboxypeptidase and elastase; anionic, non-ionic and zwitterionic detergents such as SDS, lithium dodecyl sulfate (LDS), polyethylene glycol sorbitan monolaurate (i.e., Tween® 20), polyethylene glycol sorbitan monooleate (i.e., Tween® 80), NP-40, dodecyl trimethyl ammonium bromide (DTAB), cetyl trimethyl ammonium bromide (CTAB), 3 [(3-cholamidopropyl)dimethylammonio]-1-propanesulfonate (CHAPS), polyethylene glycol tert-octylphenyl ether (i.e., Triton X detergents such as Triton X-20 and Triton X-100); surfactants such as surfactin; solvents such as phenol, chloroform, and isoamylalcohol; amides such as N-ethylacetamide, N-butylacetamide and N,N-dimethyl-acetamide; reducing agents such as glutathione, β-mercaptoethanol and dithiothereitol (DTT); protein denaturing salts such as NaCl, KCl, $LiC_1$, $NH_4Cl$, $(NH_4)_2SO_4$ and perchlorate salt; and agents that cause an increase in pH such as KOH, NaOH, $NH_4OH$ and $Ca(OH)_2$. Proteolytic enzymes are generally preferred as the protein denaturant, and ProK is exemplary of such proteolytic enzymes. The usefulness of any protein denaturant in the method of the present invention may be readily ascertained by one skilled in the art using routine screening methods that do not require undue experimentation.

When used in the methods of the present invention, the concentration of the protein denaturants can vary depending on other agents and conditions, but is sufficient to disrupt the protein membranes or walls of cells, virions, DNase or RNase, causing protein denaturation and organism lysis and releasing nucleic acid in biological samples in the presence of other protein denaturants and/or aprotic solvents. This concentration of protein denaturant can be readily determined by those skilled in the art using routine screening methods that do not require undue experimentation. When ProK is used as the protein denaturant with at least one aprotic solvent, the desirable concentration of ProK depends on the proteinaceous content of the biological samples. For most biological samples, it is in the range of about 1 to about 100 units per milliliter of biological sample. However, some biological samples may require dilution or concentration prior to the pretreatment in order to make use of ProK in its optimal concentration range, i.e., about 1 to about 100 units per milliliter of biological sample. When a base or a salt is used as the protein denaturant, for most biological samples, the concentration of the base or salt is in the range of about 10 to about 400 mM, more preferably about 80 to about 220 mM, and most preferably about 100 mM. When a detergent is used as the protein denaturant, for most biological samples, the concentration of the detergent is in the range of about 0.05% to about 8.0%, more preferably about 0.05% to about 4%, and most preferably about 1%.

More than one protein denaturant can be utilized for the pretreatment according to the present invention. The combinations of the same type or different types of protein denaturants offer additional advantages in the pretreatment of biological samples for the extraction of nucleic acids. The concentrations of mixed protein denaturants in the method of the present invention can also be readily ascertained by one skilled in the art using routine screening methods that do not require undue experimentation.

In one embodiment, one or more aprotic solvents are utilized with the protein denaturant(s). The aprotic solvent used in the present invention is capable of dissolving ionic substances because of the permanent or induced dipole, which allows the formation of an ion-dipole force. Aprotic solvents do not donate suitable hydrogen atoms to form labile hydrogen bonds with anions. Nucleophilic substitution by the SN2 mechanism with a charged nucleophile is often faster in aprotic solvents.

The dipolar aprotic solvent is a solvent with a comparatively high relative permittivity (or dielectric constant),e.g., greater than about 15, and a dipole moment. However, unlike water, the more common polar solvent, aprotic solvents do not ionize to form hydrogen ions, which confers advantages.

Aprotic solvents useful in the present invention include formamide, dimethylformamide (DMF), dimethyl sulfoxide (DMSO), dimethylacetamide (DMAC), acetonitrile, benzene, toluene, acetone, cyclohexane, n-heptane, sulfur dioxide, hexamethylphosphoramide (HMPA) and other nonaqueous media that can be used to denature and solubilize the target nucleic acid. Formamide is a preferred aprotic solvent. Such aprotic solvents are well known in the art and may be purchased from known vendors or synthesized using well-known standard techniques. The usefulness of any aprotic solvent in the method of the present invention may be readily ascertained by one skilled in the art using routine screening methods that do not require undue experimentation.

When used in the method of the present invention, the concentration of the aprotic solvent can vary depending on other agents and conditions, but is sufficient to protect a nucleic acid by maintaining the nucleic acid in solution at the required temperature and in the presence of at least one protein denaturant. This concentration can be readily determined by those skilled in the art using routine screening methods that do not require undue experimentation. When formamide is the aprotic solvent used in the method of the present invention, for most biological samples, the concentration of formamide is preferably in the range of about 10% to about 80% by volume of the reaction mixture, more preferably about 20% to about 40%, and most preferably about 30%.

More than one aprotic solvent can be utilized for the pretreatment according to the present invention. The combinations of different aprotic solvents offer additional advantages in the pretreatment of biological samples for the extraction of nucleic acid therefrom. The concentrations of mixed aprotic solvents in the methods of the present invention can also be readily ascertained by one skilled in the art using routine screening methods that do not require undue experimentation.

The temperatures at which the methods of the present invention are conducted are generally described as at or above about 4° C., preferably at or above about 25° C. A more preferred range is from about 55° C. to about 95° C. An even more preferred range of temperature is about 65° C. to about 85° C. The most preferred temperature is about 70° C. It is believed that the high temperature contributes to the denaturation of proteins in the method of the present invention.

In another embodiment of the invention, stepwise heating is utilized with protein denaturant(s) alone or in combination with aprotic solvent(s) for extraction of nucleic acid from biological samples. Stepwise heating is a heating procedure that increases or decreases the treatment temperature systematically by two or more steps for the extraction of nucleic acid from biological samples. For example, twenty-minute treatments at each treatment temperature of 55° C. and 85° C. are utilized for the protein denaturation and nucleic acid extraction with the proteolytic enzyme, Pro K. Stepwise heating has shown improved recoveries for nucleic acid extraction. The temperature ranges and the duration of the heating steps in the method of the present invention can be readily ascertained by one skilled in the art using routine screening methods that do not require undue experimentation.

In yet another embodiment of the present invention, sample dilution with an aqueous solution or an aprotic solvent is utilized with protein denaturant(s) alone or with aprotic solvent(s). The aqueous solution can be water or any buffer solution with a pH value between about 3.0 to about 10.0. The sample dilution has shown improved recoveries for nucleic acid extraction. The dilution step brings about further protein denaturation and/or precipitation while maintaining the nucleic acid in solution. The dilution factor (reaction mixture/diluent) is usually between 4:1 and 1:10 depending on the sample, the diluent and the treatment condition. The choice of diluent and dilution factor for use in the method of the present invention can be readily determined by one skilled in the art using routine screening methods that do not require undue experimentation.

Yet another aspect of the present invention is to provide kits for treating a biological sample for the extraction of nucleic acid therefrom, wherein the kits comprise at least one protein denaturant with or without one or more aprotic solvents as described herein. The kits may contain water and buffer solutions as described herein, as well as iron oxide or other solid supports for nucleic acid purification, which are described in more detail elsewhere. The kits may also contain one or more of the following items for processing and assaying the biological samples: collection devices such as swabs, tubes and pipettes; controls; pH indicators; and thermometers. Kits may include containers of reagents mixed together in suitable proportions for performing the method in accordance with the present invention. Reagent containers preferably contain reagents in unit quantities that obviate measuring steps when performing the subject method.

The present invention also includes the reaction mixtures, as well as methods of extracting nucleic acid from the reaction mixtures. The reaction mixtures comprise at least one protein denaturant and with or without one or more aprotic solvents. The reaction mixtures may in some embodiments include various reagents used with the subject reaction mixtures to purify and detect nucleic acids, such as buffers and iron oxide or other solid supports for nucleic acid purification.

The invention will now be described in greater detail by way of the specific examples. The following examples are offered for illustrative purposes and are not intended to limit the invention in any manner. In these examples, the reversible binding of nucleic acid molecules on paramagnetic particles in an acidic environment, as disclosed in U.S. Pat. No. 5,973,138 to Collis, which is incorporated herein by reference, is used for nucleic acid isolation from the reaction mixture resulting from treating samples for extraction of intact nucleic acid according to the present invention. The binding pH is preferably about 1 to about 6.5, more preferably about 1 to about 4, and most preferably about 2. The elution pH is preferably about 6.5 to about 12, more preferably about 7.5 to about 11, and most preferably about 8. The paramagnetic iron oxide technology captures nucleic acids non-specifically, or independent of sequence. There are several other automated nucleic acid extraction technologies currently on the market, representing both specific and non-specific capture. The most notable non-specific capture systems include the Roche MagNA Pure LC and the Organon Teknika Nuclisens, both of which utilize magnetic silica particles. The Qiagen BioRobot 9604 incorporates silica membranes. The Roche AmpliPrep captures targets specifically with streptavidin-coated magnetic particles and biotinylated capture probes. GenProbe's Tigris system is expected to utilize oligonucleotide-coated magnetic particles. In addition, materials such as iron oxide, silica-coated particles, silica-coated membranes, glass fiber mats, glass membranes and other glasses, zeolites and ceramics can also be used as a solid phase binding surface for nucleic acid extraction. In summary, any conventional effective technique for nucleic acid isolation and purification known in the art, including liquid and solid phase separation, can be utilized for the isolation and purification of nucleic acids following the pretreatment process of the present invention or, alternatively, the pretreatment process may be performed in the presence or absence of conventional effective techniques for nucleic acid isolation and purification that are known in the art.

Strand displacement amplification (SDA) is also utilized in these examples for amplification and detection of the target nucleic acid sequence following the extraction process of the invention and any appropriate isolation or purification step. The SDA method involves first mixing single-stranded target sequences with a nucleic acid polymerase, restriction endonuclease, deoxynucleoside triphosphates and at least one primer, which is complementary to a region at the 3' end of a target fragment, wherein each primer has a sequence at the 5' end that is a recognition sequence for a restriction endonuclease, and then allowing the mixture to react for a time sufficient to generate reaction products. Where the nucleic acids comprise RNA, it is preferable to use reverse transcriptase to convert RNA to cDNA. The invention, however, is not limited to SDA detection, and many conventional and effective detection techniques such as hybridization and polymerase chain reaction (PCR) may be used for detection following the pretreatment process of the invention.

The following examples illustrate the effectiveness of the pretreatment process of the present invention to pretreat whole blood and plasma samples for nucleic acid extraction. Whole blood and plasma are among the most challenging samples for nucleic acid extraction because of their highly proteinaceous content; therefore, the methods of the present invention are expected to be effective for other biological samples as well. Representative examples are discussed herein.

EXAMPLE 1

Evaluation of Plasma Pretreatment at Varying Temperatures

The experiment was designed to evaluate the effect of temperature during the ProK plasma pretreatment of the present invention on extraction of RNA. The RNA was extracted from the sample using iron oxide.

First, 40 mg of iron oxide and 1200 uL of 30 mM potassium phosphate buffer (KPB) were dispensed into eight 2 mL polypropylene tubes. Plasma (600 uL), anti-coagulated with EDTA was added to six of the tubes, and 600 uL of 30 mM KPB was added to the remaining two tubes. Three units of ProK were then added to each tube, and the tubes were mixed. The two tubes containing KPB and two of the tubes containing plasma were incubated at room temperature for 20 minutes. Two tubes containing plasma were incubated at 37° C. for 20 minutes, and two tubes containing plasma were incubated at 52° C. for 20 minutes. Following incubation, 180 uL of 6 M glycine/HCl, 1 ug of carrier RNA and 5000 HIV in vitro transcripts were added to each tube. The tubes were then mixed for 15 minutes by alternately turning electromagnets, positioned on opposite sides of the tubes, on and off. This mixed the samples by drawing the iron oxide particles back and forth through the solution. The iron oxide particles were then magnetically locked to the sides of the tubes by turning on the electromagnets. The unbound sample from each tube was then removed by aspiration. The particles were then washed twice with 2 mL of 90 mM glycine/HCl. The tubes were then mixed, the particles were locked to the side, and the fluid removed by aspiration as described above. The samples were eluted from the iron oxide in each tube by adding 0.4 mL of elution buffer composed of 45 mM KOH, 90 mM Bicine, and 20 mM $KPO_4$ and mixing the tubes. Following elution, the eluents were transferred to new tubes by magnetically locking the iron oxide particles to the side and aspirating the sample into new tubes. Next, 1 ug of yeast carrier RNA was added to each tube. The eluted samples were then assayed by SDA using an HIV reverse transcriptase (RT)-SDA assay system. The results were as follows:

| Plasma (uL) | Temperature | Mean Signal |
|---|---|---|
| 0 | 25° C. | 95,969 |
| 600 | 25° C. | 41,410 |
| 600 | 37° C. | 5,896 |
| 600 | 52° C. | 46,709 |

The signal responses at various temperatures indicate RNA target recoveries when plasma is pretreated with ProK at temperatures as high as 52° C.

EXAMPLE 2

Evaluation of Plasma Pretreatment at High ProK Concentration and Temperature The following experiment examined the effect of varying ProK concentrations and high temperature plasma pretreatment on extraction of RNA. The samples were extracted using iron oxide.

EDTA anti-coagulated plasma (600 uL) collected in PPT™ tubes from Becton Dickinson (BD) was transferred to new tubes, each containing 40-45 mg iron oxide. Following transfer, 220 uL of 30 mM KPB was added to each of the tubes. Next, 3, 6, or 9 units of ProK was added to the tubes, and the tubes were then incubated for 20 minutes in a 55° C., 65° C., or 75° C. water bath. Following incubation, 180 uL of 6 M glycine/HCl was added to each tube, and the tubes were mixed by aspirating up and down with a pipette. Yeast carrier RNA (10 uL of 10 ug/mL) was added to each tube. The samples were then spiked with 6 uL of $10^7$ copies/mL HIV RNA in vitro transcript. The samples were mixed by aspirating and dispensing 800 uL at a time, repeated 24 times. Following mixing, the samples were then extracted as described in Example 1, i.e., by magnetically locking the iron oxide particles to the sides of the tubes and aspirating the unbound samples. The particles were washed twice with 1 mL of 86 mM glycine/HCl by aspirating and dispensing 800 uL for a total of 12 times, locking the iron oxide particles to the side of the tubes, and aspirating the fluid from tubes. The sample was then eluted from the iron oxide by adding 0.4 mL of elution buffer composed of 90 mM Bicine, 50 mM KOH, and 20 mM $KPO_4$ to each tube, mixing by aspirating and dispensing 300 uL 12 times. Following elution, 10 microliters of yeast carrier RNA (10 mg/mL) was added to each tube. The tubes were then heated to 60° C. while being subjected to magnetic mixing for 20 minutes by alternately turning electromagnets, positioned on opposite sides of the tubes, on and off. This mixed the samples by drawing the iron oxide particles back and forth through the solution. The eluted samples were transferred to new tubes as described in Example 1, i.e., by magnetically locking the iron oxide particle to the side and aspirating the sample into new tubes and, assayed by SDA using an HIV reverse transcriptase (RT)-SDA assay system. The results are as follows:

| Sample | Temperature | Proteinase K | Mean Signal |
|---|---|---|---|
| Clean | 55° C. | 9 U | 2,883 |
|  | 65° C. | 6 U | 54,824 |
|  | 75° C. | 3 U | 71,577 |
| Plasma | 55° C. | 3 U | 1,759 |
|  |  | 6 U | 13,611 |
|  |  | 9 U | 12,356 |
|  | 65° C. | 3 U | 8,241 |
|  |  | 6 U | 23,029 |
|  |  | 9 U | 20,961 |
|  | 75° C. | 3 U | 17,650 |
|  |  | 6 U | 12,767 |
|  |  | 9 U | 19,554 |

The results demonstrate that the pretreatment of plasma with 6-9 units of ProK results in target recovery throughout the temperature range tested (55° C. to 75° C.). Furthermore, the correlation between the temperature and the amount of ProK shows that at higher temperatures, target recovery can be achieved throughout the ProK range tested (3-9 units of ProK).

EXAMPLE 3

Evaluation of Plasma Pretreatment with Formamide and Varying Thermal Profiles The following experiment examined the effect of ProK and formamide and varying thermal profiles during plasma pretreatment on extraction of RNA. The RNA was extracted from the sample using iron oxide.

First, 500 uL of EDTA anti-coagulated plasma was added to 64 tubes, each containing 40-45 mg of iron oxide. Eight of these tubes were set aside as controls, i.e. were not pretreated.

Phosphate buffered saline (PBS) (300 uL) was added to eight of the tubes. The remaining forty-eight tubes received 300 uL of formamide. To each of the fifty-six tubes that contained either PBS or formamide, 20 units of ProK was added. The tubes were incubated at the temperatures and times specified in the summary table. All of the tubes were then spiked with 2,500 copies of HIV in vitro transcript to simulate a plasma sample containing 5,000 copies/mL HIV RNA. Next, 180 uL of 6 M glycine/HCl was added to each tube, and the samples were mixed by aspirating 800 uL up and down with a pipette for a total of 24 times. The iron oxide particles were then magnetically locked to the sides of the tubes, and the unbound samples were removed by aspiration. The particles were washed twice with 1 mL of 90 mM glycine/HCl by aspirating and dispensing 800 uL for a total of 12 times. After each wash, the particles were locked to the sides of the tubes and the fluid was removed by aspiration from each tube. The samples were eluted from the particles with the addition of 120 uL of elution buffer composed of 75 mM Bicine, 85 mM KOH and mixing by aspirating and dispensing 100 uL at a time for a total of 15 times. The samples were then neutralized by adding 60 uL of neutralization buffer composed of 400 mM Bicine to each tube and mixed by aspirating and dispensing 100 uL at a time for a total of 15 times. The eluted samples were transferred to new tubes as described in Example 1. The eluted samples were assayed by SDA using an HIV RT-SDA assay system. The results are as follows:

| Pretreatment Reagents | Pretreatment Incubation(s) | Mean Signal |
| --- | --- | --- |
| None | None | 8597 |
| ProK/PBS | 20 min. @ 75° C. | 4398 |
| ProK + Formamide | 20 min. @ 85° C. | 37948 |
| ProK + Formamide | 20 min. @ 65° C. + 10 min. @ 70° C. | 100894 |
| ProK + Formamide | 20 min. @ 65° C. + 10 min. @ 85° C. | 63822 |
| ProK + Formamide | 30 min. @ 70° C. | 99491 |
| ProK + Formamide | 20 min. @ 70° C. | 74560 |

The results clearly demonstrate that pre-treating plasma with ProK and formamide for the times and temperatures described gives significantly higher mean signals than not pretreating or by pretreating with ProK and PBS for 20 minutes at 75° C.

EXAMPLE 4

Evaluation of DNA Extraction from Plasma, with and without Iron Oxide Present During Plasma Pretreatment The following experiment was conducted to compare DNA extraction efficiency from plasma when iron oxide is present during plasma pretreatment versus iron oxide being added after pretreatment.

Human plasma (500 uL) was added to each of twelve 2 mL tubes—six containing 40 mg iron oxide and six empty tubes. ProK (5 units) was added to each tube, and the tubes were incubated for 20 minutes at 65° C. Formamide (400 uL) was added, and the tubes were incubated for 10 minutes at 70° C. The samples that were pretreated without iron oxide were transferred to six new 2 mL tubes containing 40 mg iron oxide. Next, 2,500 copies of K10 DNA plasmid containing an *M. tuberculosis* (TB) specific sequence were spiked into five of the six tubes that were pretreated without iron oxide present and into five of the six tubes that were pretreated with iron oxide present. To each tube was added 180 uL of 6 M glycine/HCl, followed by mixing by aspirating up and down. The iron oxide particles were magnetically locked to the sides of the tubes, and the unbound samples were aspirated. Tubes were washed twice with 5 mM glycine/HCl, locking particles to sides of tubes after each wash and aspirating fluid from tubes. Elution buffer (120 uL) composed of 105 mM KOH and 14% DMSO was added and mixed by pipetting up and down. The eluted samples were then transferred to new tubes as described in Example 1. Neutralization buffer (60 uL) composed of 350 mM Bicine and 38.5% glycerol was added and mixed by pipetting up and down. Eluted samples were amplified in a Direct TB SDA assay (DTB) to obtain DTB specific response and internal amplification control (IC) response. The results are as follows:

| Pretreatment Condition | Target | Mean DTB Signal | Mean IC Signal |
| --- | --- | --- | --- |
| No iron oxide at pretreatment | 0 K10/sample | 7 | 30639 |
| | 2500 K10/sample | 33810 | 20214 |
| 40 mg iron oxide at pretreatment | 0 K10/sample | 0 | 19898 |
| | 2500 K10/sample | 2966 | 32178 |

The results demonstrate that combining plasma and iron oxide after plasma pretreatment, rather than before pretreatment, improves DNA extraction efficiency from plasma as indicated by signal improvement in the TB amplification assay.

EXAMPLE 5

Evaluation of DNA Extraction from Plasma, with and without Iron Oxide Present During Plasma Pretreatment, and with and without AC Field Applied During Mixing The following experiment was conducted to compare DNA extraction efficiency from plasma when iron oxide is present during plasma pretreatment versus when iron oxide was added after pretreatment and to examine the two conditions with and without an alternating current (AC) field during mixing.

Human plasma (500 uL) was added to each of twenty-four 2 mL tubes containing 40 mg iron oxide and to twenty-four empty 2 mL tubes. ProK (5 units) and 300 uL formamide were added to each tube. All tubes were incubated for 20 minutes at 65° C. and then for 10 minutes at 85° C. The samples that were pretreated without iron oxide were transferred to new 2 mL tubes containing 40 mg iron oxide. Next, 4,000 copies of K10 DNA plasmid containing an *M. tuberculosis* (TB) specific sequence was spiked into 20 of the 24 tubes that were pretreated without iron oxide present and into 20 of the 24 tubes that were pretreated with iron oxide present. Then, 150 uL of 6 M glycine/HCl was added and mixed by aspirating up and down. Twelve of the tubes pretreated with iron oxide present and 12 of the tubes pretreated without iron oxide present were mixed without an AC field at each mix step. The remaining 12 tubes pretreated with iron oxide present, as well as the remaining 12 tubes pretreated without iron oxide present, were mixed under a 30 mV AC field at each mix step. The iron oxide particles were magnetically locked to the sides of the tubes, and the unbound sample was aspirated from the tubes. The tubes were washed twice with 5 mM glycine/HCl, locking particles to sides of tubes after each wash and aspirating fluid from tubes. Next, 120 uL of elution buffer composed of 105 mM KOH and 14% DMSO was added and mixed by pipetting up and down. The eluted samples were transferred to new tubes as in Example 1. Neutralization buffer (60 uL) composed of 350 mM Bicine and 38.5% glycerol was added and mixed by pipetting up and down. Eluted samples were amplified in the Direct TB SDA assay to obtain DTB specific response and IC response. The results are as follows:

| Pretreatment Cond. | AC at Mixing | Target | Mean DTB Signal | Mean IC Signal |
|---|---|---|---|---|
| No iron oxide | None | 0 K10/sample | 0 | 45599 |
| | | 4000 K10/sample | 41428 | 40049 |
| | 30 mV | 0 K10/sample | 4 | 37409 |
| | | 4000 K10/sample | 69126 | 33033 |
| 40 mg iron oxide | None | 0 K10/sample | 0 | 51567 |
| | | 4000 K10/sample | 10470 | 44495 |
| | 30 mV | 0 K10/sample | 0 | 32879 |
| | | 4000 K10/sample | 7820 | 36261 |

The results demonstrate that combining plasma and iron oxide after plasma pretreatment, rather than before pretreatment, improves DNA extraction efficiency from plasma as indicated by signal improvement in the TB amplification assay. Mixing in the presence of the AC field improved signal for samples that did not contain iron oxide during pretreatment.

EXAMPLE 6

Evaluation of the Effect of Diluting Plasma Sample Prior to ProK Digestion Versus after ProK Digestion on DNA Extraction from Plasma with Iron Oxide The following experiment was conducted to compare DNA extraction efficiency from plasma with iron oxide when plasma is diluted prior to ProK digestion with potassium phosphate buffer versus diluted after ProK digestion with water.

Human plasma (500 uL) was added to each of twenty-four 2 mL tubes. ProK (5 units) and 400 uL of 30 mM potassium phosphate buffer were added to eight of the plasma tubes and incubated for 20 minutes at 65° C. followed by incubation for 10 minutes at 70° C. ProK (9 units) and 400 uL of 30 mM potassium phosphate buffer were added to eight of the plasma tubes and incubated for 20 minutes at 65° C. followed by incubation for 10 minutes at 70° C. ProK (5 units) was added to eight of the plasma tubes and incubated for 20 minutes at 65° C. Following the 65° C. incubation, these tubes were diluted with 400 uL of water and incubated for 10 minutes at 70° C. Potassium phosphate buffer (900 uL) was added to the remaining eight 2 mL tubes. Each of the solutions were transferred to new 2 mL tubes containing 40 mg iron oxide each. Next, 3,000 copies of K10 DNA plasmid containing an *M. tuberculosis* specific sequence was spiked into six of the eight tubes of each of the four conditions. The remaining two tubes of each condition were left as negative controls. Next, 180 uL of 6 M glycine/HCl was added to each tube and mixed by aspirating up and down. The iron oxide particles were magnetically locked to the sides of the tubes, and the unbound samples were aspirated. The tubes were washed twice with 5 mM glycine/HCl, locking particles to the sides of tubes after each wash and aspirating fluid from tubes. Elution buffer (120 uL) composed of 105 mM KOH and 14% DMSO was added and mixed by pipetting up and down. The eluted samples were transferred to new tubes as described in Example 1. Neutralization buffer (60 uL) composed of 350 mM Bicine and 38.5% glycerol was added and mixed by pipetting up and down. Eluted samples were amplified in the Direct TB SDA assay to obtain DTB specific response and IC response. The results are as follows:

| Sample | Dilution | Target | Mean DTB Signal | Mean IC Signal |
|---|---|---|---|---|
| Buffer | N/A | 0 K10/sample | 0 | 43048 |
| | | 3000 K10/sample | 28611 | 42912 |
| Plasma | Pre-ProK (5 U) | 0 K10/sample | 15 | 48233 |
| | | 3000 K10/sample | 2984 | 50713 |
| | Pre-ProK (9 U) | 0 K10/sample | 1 | 46930 |
| | | 3000 K10/sample | 13126 | 50987 |
| | Post-ProK (5 U) | 0 K10/sample | 45 | 52543 |
| | | 3000 K10/sample | 22893 | 49802 |

The results demonstrate that diluting the plasma following ProK digestion improves DNA extraction efficiency from plasma as indicated by increased signal in the TB amplification assay. Results from the post-ProK dilution condition approach those of the buffer sample control.

EXAMPLE 7

Evaluation of Formamide and Water as Plasma Diluents in DNA Extraction with Iron Oxide The following experiment was conducted to compare DNA extraction efficiency from plasma with iron oxide when plasma is diluted after ProK digestion with either formamide or water.

To each of twelve 2 mL tubes was added 500 uL human plasma and 5 units of ProK. The tubes were incubated for 20 minutes at 65° C. Formamide (400 uL) was added to six of the tubes, and the tubes were incubated for 10 minutes at 70° C. Water (400 uL) was added to the remaining six tubes, and the tubes were incubated for 10 minutes at 70° C. Each of the solutions were transferred to new 2 mL tubes containing 40 mg iron oxide each. Next, 2,500 copies of K10 DNA plasmid, containing an *M. tuberculosis* specific sequence were spiked into five of the six tubes of each of the two conditions. The remaining tube of each condition was left as a negative control. Next, 180 uL of 6 M glycine/HCl was added to each of the tubes and mixed by aspirating up and down. The iron oxide particles were magnetically locked to the sides of the tubes, and the unbound samples were aspirated from the tubes. The tubes were washed twice with 5 mM glycine/HCl, locking particles to the sides of tubes after each wash and aspirating fluid from tubes. Elution buffer (120 uL) composed of 105 mM KOH and 14% DMSO was added and mixed by pipetting up and down. The eluted samples were transferred to new tubes as described in Example 1. Neutralization buffer (60 uL) composed of 350 mM Bicine and 38.5% glycerol was added and mixed by pipetting up and down. Eluted samples were amplified in the Direct TB SDA assay to obtain DTB specific response and IC responses. The results are as follows:

| Diluent | Target | Mean DTB Signal | Mean IC Signal |
|---|---|---|---|
| Formamide | 0 K10/sample | 0 | 47601 |
| | 3000 K10/sample | 36305 | 41066 |
| Water | 0 K10/sample | 0 | 50143 |
| | 3000 K10/sample | 41650 | 28297 |

The results demonstrate that diluting the plasma following ProK digestion with either water or formamide yields similar DNA extraction efficiency from plasma as indicated by similar signal in the TB amplification assay.

EXAMPLE 8

Evaluation of Varying Carrier RNA Concentrations on Recovery of RNA from Plasma with Iron Oxide The following experiment was conducted to evaluate the effect of increasing yeast carrier RNA concentrations on RNA extraction from plasma with iron oxide.

Human plasma was spiked with 10,000 HIV particles per mL, and 500 uL of HIV-spiked plasma was added to forty 2 mL tubes. ProK (40 units) was added to each tube. Next, 300 uL of 30 mM KP containing 0, 2.5, 5, 10, or 20 ug carrier RNA was added to the tubes (eight tubes per carrier RNA level). Given a 0.5 mL plasma sample, this translates into carrier RNA concentrations of 0, 5, 10, 20, and 40 ug per mL plasma. To serve as RNA controls, 500 uL non-spiked plasma, 40 units of ProK, 300 uL of formamide and 10,000 copies of HIV in vitro transcript were added to eight 2 mL tubes. All tubes were incubated for 30 minutes in a 70° C. water bath. Next, 180 uL of 6 M glycine/HCl was added and mixed by aspirating and dispensing 800 uL 24 times. The iron oxide particles were magnetically locked to the sides of the tubes, and the unbound samples were aspirated. The tubes were washed twice with 1 mL of 6 mM glycine/HCl by aspirating and dispensing 800 uL 15 times. The particles were locked to the side, and fluid was aspirated from the tubes. Elution buffer (120 uL) composed of 75 mM Bicine, 85 mM KOH, and 30 mM $KPO_4$ was added to each tube and mixed by aspirating and dispensing 100 uL 15 times. The eluted samples were transferred to new tubes as described in Example 1. Neutralization buffer (60 uL) composed of 400 mM Bicine was added to each tube and mixed by aspirating and dispensing 100 uL 15 times. The iron oxide particles were magnetically locked to the sides of the tubes to allow for removal of eluted sample. The eluted samples were amplified in a HIV RT-SDA assay. The results are as follows:

| Target | CRNA/mL Plasma | Mean Signal |
| --- | --- | --- |
| HIV Particles | 0 ug | 10577 |
| HIV Particles | 2.5 ug | 12412 |
| HIV Particles | 5.0 ug | 18008 |
| HIV Particles | 10.0 ug | 18959 |
| HIV Particles | 20.0 ug | 21910 |
| HIV in vitro transcript | 0 ug | 21962 |

The results demonstrate that the presence of carrier RNA improves recovery of specific RNA target from plasma. Carrier RNA was previously titrated into the HIV amplification assay up to 20 ug and shown to have no effect on amplification.

EXAMPLE 9

ProK Pretreatment of Plasma with Stepwise Heating for Nucleic Acid Extraction

The following experiment was conducted to examine the effects of activating ProK at 55° C. or 65° C. followed by a 20 minute incubation at 75° C. before binding RNA in the iron oxide system.

A volume of 600 uL plasma from BD PPT™ tubes was added to tubes containing 40-45 mg iron oxide, and then 220 uL of 30 mM $KPO_4$ was added to each of the tubes. ProK (6 units) was also added to each tube, and the ProK was activated by incubating the tubes for 20 minutes either in a 55° C. water bath or in a 65° C. water bath. The tubes were transferred to a 75° C. water bath and incubated for 20 minutes. The samples were cooled at room temperature for 5 minutes. Next, 180 uL of 6 M glycine/HCl was added to each tube, and the samples were pipette mixed. Next, 10 uL yeast carrier RNA (10 ug/mL) was added to each tube, followed by 6 uL HIV stock RNA ($10^7$ copies/ml) and pipette mixed. The unbound samples were removed from the tubes by locking iron oxide particles to the side of tube and aspirating the solution to waste. The particles were washed three times with 1000 uL wash solution (86 mM glycine/HCl) by pipette mixing, locking iron oxide particles to the side of each tube, and aspirating unbound solution. The samples were then eluted by adding 400 uL elution buffer (90 mM Bicine, 50 mM KOH and 20 mM $KPO_4$) to each tube and conducting 12 cycles of aspiration mixing, followed by 20 minutes of magnetic mixing at 60° C., followed by a second round of 12-cycle aspiration mixing. Yeast carrier RNA (10 ug) was added to each tube. The target was added to pre-assay spiked control samples. The samples were removed to new tubes as described in Example 1 and assayed by an HIV RT-SDA assay. The results are as follows:

| Specimen | Buffer | Plasma | Buffer | Plasma |
| --- | --- | --- | --- | --- |
| Pro K | 6 U | 6 U | 6 U | 6 U |
| Pro K Activation | 55° C. | 55° C. | 65° C. | 65° C. |
| Pro K Incubation | 75° C. | 75° C. | 75° C. | 75° C. |
| Signal | 49816 | 6182 | 28052 | 70729 |
|  | 52798 | 31904 | 74120 | 73942 |
|  | 56186 | 53210 | 76484 | 58029 |
|  | 55034 | 57928 | 67257 | 51201 |
| Mean Signal | 53459 | 37306 | 61478 | 63475 |
| % CV | 5 | 63 | 37 | 17 |

The pretreating of plasma with ProK at elevated temperatures (55° C. to 65° C. activation temperature followed by 75° C. incubation temperature) demonstrates extraction efficiency as indicated by positive assay signals.

EXAMPLE 10

RNA Extraction from Whole Blood

This experiment was conducted to extract RNA from whole blood and examine the use of additional wash steps to decrease carryover of inhibitory components into the elution step.

Whole blood samples (500 uL) were each pretreated with 20 units of ProK and 300 uL of formamide for 20 minutes at 65° C. and 10 minutes at 85° C. One set of samples was pretreated with a 6-cycle wash for two washes and another set with a 9-cycle wash for three washes. The samples were eluted with 85 mM KOH/75 mM Bicine, neutralized with 400 mM Bicine, and detected with in the HIV gag gene RT-SDA amplification system. The results are as follows:

| | Wash | | | |
|---|---|---|---|---|
| | 2X WASH and 6 CYCLES | | 3X WASH and 9 CYCLES | |
| COPIES/ML | Signal | Mean Signal | Signal | Mean Signal |
| 0 | 64 | | 241 | |
| 0 | 35 | | 151 | |
| 0 | 27 | | 474 | |
| 0 | 119 | 61 | 57 | 231 |
| 5,000 | 6798 | | 1151 | |
| 5,000 | 22268 | | 2433 | |
| 5,000 | 2831 | | 4031 | |
| 5,000 | 42 | 7985 | 45 | 1915 |
| 25,000 | 11154 | | 30543 | |
| 25,000 | 7470 | | 53000 | |
| 25,000 | 23408 | | 42699 | |
| 25,000 | 20112 | 15536 | 39496 | 41435 |
| 50,000 | 9982 | | 35527 | |
| 50,000 | 47798 | | 81777 | |
| 50,000 | 15862 | | 27265 | |
| 50,000 | 7165 | 20202 | 53345 | 49479 |

The results demonstrate that the additional wash improves assay signal indicating reduced carryover of inhibitory substances with increased washing.

While the invention has been described with some specificity, modifications apparent to those with ordinary skill in the art may be made without departing from the scope of the invention. Various features of the invention are set forth in the following claims.

What is claimed is:

1. A method of treating a biological sample to solubilize and extract nucleic acids therefrom comprising treating the sample with at least one protein denaturant and at least one aprotic solvent,
    wherein the at least one aprotic solvent is selected from the group consisting of formamide, dimethylformamide, dimethyl sulfoxide, dimethylacetamide, acetronitrile, benzene, toluene, acetone, cyclohexane, n-heptane, sulfur dioxide and hexamethylphosphoramide,
    wherein the at least one protein denaturant is a proteolytic enzyme selected from the group consisting of proteinase K, pronase, pepsin, trypsin, chymotrypsin, carboxypeptidase and elastase, and
    wherein the method is carried out at a temperature at or above 4° C.

2. The method of claim 1 wherein the at least one protein denaturant further comprises a second protein denaturant selected from the group consisting of proteolytic enzymes, detergents, surfactants, solvents, amides, reducing agents, bases, protein denaturing salts and combinations thereof.

3. The method of claim 1 wherein the proteolytic enzyme is proteinase K.

4. The method of claim 2 wherein the second protein denaturant is a detergent selected from the group consisting of sodium dodecyl sulfate, lithium dodecyl sulfate, polyethylene glycol sorbitan monolaurate, polyethylene glycol sorbitan monooleate, NP-40, dodecyl trimethyl ammonium bromide, cetyl trimethyl animonium bromide, 3[(3-cholamidipropyl)dimethylammonio]-1-propanesulfonate and polyethylene glycol tert-octylphenyl ether.

5. The method of claim 2 wherein the second protein denaturant is a surfactant.

6. The method of claim 2 wherein the second protein denaturant is a solvent selected from the group consisting of phenol, chloroform and isoamylalcohol.

7. The method of claim 2 wherein the second protein denaturant is an aniide selected from the group consisting of N-ethylacetamide, N-butylacetamide and N,N-dimethylacetamide.

8. The method of claim 2 wherein the second protein denaturant is a reducing agent selected from the group consisting of glutathione, β-mercatoethanol and dithiothreitol.

9. The method of claim 2 wherein the second protein denaturant is a base selected from the group consisting of KOH, NaOH, $NH_4OH$ and $Ca(OH)_2$.

10. The method of claim 2 wherein the second protein denaturant is a protein denaturing salt selected from the group consisting of NaCl, KCl, LiCl, $NH_4Cl$, $(NH_4)_2SO_4$ and perchlorate salt.

11. The method of claim 1 wherein the at least one aprotic solvent is selected from the group consisting of dimethylacetamide, acetronitrile, beuzene, toluene, acetone, cyclohexane, n-heptane, sulfur dioxide and hexamethylphosphoramide.

12. The method of claim 1 wherein the aprotic solvent is fonnamide.

13. The method of claim 1 wherein the method is carried out in a temperature range of about 25° C. to about 95° C.

14. The method of claim 1 wherein the method is carried out in a temperature range of about 65° C. to about 85° C.

15. The method of claim 1 wherein the method is carried out by stepwise heating in a temperature range of about 55° C. to about 85° C.

16. The method of claim 3 wherein the concentration of proteinase K is about 1 to about 100 units per milliliter of biological sample.

17. The method of claim 1 wherein the biological sample is diluted or concentrated.

18. The method of claim 12 wherein the concentration of formamide is about 10% to about 80% by volume.

19. The method of claim 1 wherein the nucleic acid is RNA.

20. The method of claim 1 wherein a reagent is both a protein denaturant and an aprotic solvent selected from the group consisting of formamide, dimethylformamide, dimethyl sulfoxide, dimethylacetamide, acetronitrile, benzene, toluene, acetone, cyclohexane, n-heptane, sulfur dioxide and hexamethylphosphoramide.

21. The method of claim 1 wherein the method comprises diluting the treated sample with a diluent selected from the group consisting of water, aqueous buffer solutions and aprotic solvents.

22. The method of claim 21 wherein the method is carried out in a temperature range of about 25° C. to about 95° C.

23. The method of claim 1 wherein the method further comprises the presence of a solid support.

24. The method of claim 23 wherein the solid support is selected from the group consisting of iron oxide, silica-coated particles, silica-coated membranes, glass fiber mats, glass membranes, glasses, zeolites and ceramics.

25. The method of claim 1 wherein the method further comprises diluting the treated sample with a diluent.

* * * * *

UNITED STATES PATENT AND TRADEMARK OFFICE
CERTIFICATE OF CORRECTION

PATENT NO. : 7,601,491 B2  Page 1 of 1
APPLICATION NO. : 10/359179
DATED : October 13, 2009
INVENTOR(S) : Collis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1683 days.

Signed and Sealed this

Fifth Day of October, 2010

David J. Kappos
*Director of the United States Patent and Trademark Office*